(12) United States Patent
Jamello et al.

(10) Patent No.: US 10,653,393 B2
(45) Date of Patent: May 19, 2020

(54) INTRAVASCULAR ULTRASOUND IMAGING WITH FREQUENCY SELECTIVE IMAGING METHODS AND SYSTEMS

(71) Applicant: ACIST Medical Systems, Inc., Eden Prairie, MN (US)

(72) Inventors: Joseph A. Jamello, Saratoga, CA (US); Kendall R. Waters, Livermore, CA (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 1173 days.

(21) Appl. No.: 14/878,246

(22) Filed: Oct. 8, 2015

(65) Prior Publication Data

US 2017/0100100 A1    Apr. 13, 2017

(51) Int. Cl.
*A61B 8/08* (2006.01)
*A61B 8/12* (2006.01)
(Continued)

(52) U.S. Cl.
CPC .......... *A61B 8/5207* (2013.01); *A61B 8/0891* (2013.01); *A61B 8/12* (2013.01);
(Continued)

(58) Field of Classification Search
CPC ....... A61B 8/5207; A61B 8/461; A61B 8/467; A61B 8/12; A61B 8/5269; A61B 8/54;
(Continued)

(56) References Cited

U.S. PATENT DOCUMENTS

| 3,918,025 A | 11/1975 | Koshikawa et al. |
| 4,347,443 A | 8/1982 | Whitney |

(Continued)

FOREIGN PATENT DOCUMENTS

| CN | 101208045 A | 6/2008 |
| CN | 103025247 A | 4/2013 |

(Continued)

OTHER PUBLICATIONS

Moore et al., "Intravascular Ultrasound Image Processing of Blood-Filled or Blood-Displaced Lumens," U.S. Appl. No. 15/704,710, filed Sep. 14, 2017, 49 pages.

(Continued)

*Primary Examiner* — Serkan Akar
(74) *Attorney, Agent, or Firm* — Fredrikson & Byron, P.A.

(57) ABSTRACT

Methods and systems for acquiring a plurality of data vectors at a first frequency and a plurality of data vectors at a second frequency, where the first frequency is greater than the second frequency. The plurality of first frequency data vectors can be formed into a first set of data vectors and the plurality of second frequency data vectors can be formed into a second set of data vectors. A first filter can be applied to the first set of data vectors to form a first modified data set and a second filter can be applied to the second set of data vectors to form a second modified data set. Based on the first and second modified data sets, a frequency response of an item in the imaging view can be determined. Using the determined frequency response of the item, an image is created on a display.

22 Claims, 8 Drawing Sheets

(51) Int. Cl.
    *A61B 8/00*     (2006.01)
    *G01S 7/52*     (2006.01)
    *G01S 15/89*     (2006.01)
    *A61M 5/00*     (2006.01)

(52) U.S. Cl.
    CPC .............. *A61B 8/461* (2013.01); *A61B 8/467* (2013.01); *A61B 8/5269* (2013.01); *A61M 5/007* (2013.01); *G01S 7/52036* (2013.01); *G01S 7/52071* (2013.01); *G01S 15/894* (2013.01); *G01S 15/8952* (2013.01); *G01S 15/8956* (2013.01); *A61B 8/4461* (2013.01); *A61B 8/54* (2013.01)

(58) Field of Classification Search
    CPC .... A61B 8/4461; A61B 8/0891; A61M 5/007; G01S 15/8952; G01S 7/52071; G01S 15/894; G01S 15/8956; G01S 7/52036
    See application file for complete search history.

(56) References Cited

U.S. PATENT DOCUMENTS

| | | | |
|---|---|---|---|
| 4,850,363 A | 7/1989 | Yanagawa | |
| 4,860,758 A | 8/1989 | Yanagawa et al. | |
| 4,949,310 A | 8/1990 | Smith et al. | |
| 5,070,734 A | 12/1991 | Kawabuchi et al. | |
| 5,070,735 A | 12/1991 | Reichert et al. | |
| 5,131,396 A | 7/1992 | Ishiguro et al. | |
| 5,183,048 A | 2/1993 | Eberle | |
| 5,203,338 A | 4/1993 | Jang | |
| 5,363,849 A | 11/1994 | Suorsa et al. | |
| 5,396,285 A | 3/1995 | Hedberg et al. | |
| 5,462,057 A | 10/1995 | Hunt et al. | |
| 5,531,679 A | 7/1996 | Schulman et al. | |
| 5,690,115 A | 11/1997 | Feldman et al. | |
| 5,741,552 A | 4/1998 | Takayama et al. | |
| 5,833,615 A | 11/1998 | Wu et al. | |
| 5,848,969 A | 12/1998 | Panescu et al. | |
| 5,876,343 A | 3/1999 | Teo et al. | |
| 5,921,931 A | 7/1999 | O'Donnell et al. | |
| 6,015,385 A | 1/2000 | Finger et al. | |
| 6,036,650 A | 3/2000 | Wu et al. | |
| 6,132,374 A | 10/2000 | Hossack et al. | |
| 6,139,501 A | 10/2000 | Roundhill et al. | |
| 6,154,572 A | 11/2000 | Chaddha | |
| 6,216,025 B1 | 4/2001 | Kruger | |
| 6,277,075 B1 | 8/2001 | Torp et al. | |
| 6,589,181 B2 | 7/2003 | Grunwald et al. | |
| 6,645,147 B1 | 11/2003 | Jackson et al. | |
| 7,194,294 B2 | 3/2007 | Panescu et al. | |
| 7,691,061 B2 | 4/2010 | Hirota | |
| 7,925,064 B2 | 4/2011 | Cloutier et al. | |
| 2001/0017941 A1 | 8/2001 | Chaddha | |
| 2001/0029336 A1 | 10/2001 | Teo | |
| 2003/0063787 A1 | 4/2003 | Natanzon et al. | |
| 2003/0078497 A1 | 4/2003 | Ji et al. | |
| 2003/0097069 A1 | 5/2003 | Avinash et al. | |
| 2003/0191392 A1 | 10/2003 | Haldeman | |
| 2003/0208123 A1 | 11/2003 | Panescu | |
| 2004/0030250 A1 | 2/2004 | Stewart | |
| 2004/0037164 A1 | 2/2004 | Garlick et al. | |
| 2004/0199047 A1 | 10/2004 | Taimisto et al. | |
| 2005/0119573 A1 | 6/2005 | Vilenkin et al. | |
| 2005/0215897 A1 | 9/2005 | Sakaguchi et al. | |
| 2005/0249391 A1 | 11/2005 | Kimmel et al. | |
| 2006/0253028 A1 | 11/2006 | Lam et al. | |
| 2007/0016068 A1 | 1/2007 | Grunwald et al. | |
| 2007/0036404 A1 | 2/2007 | Li | |
| 2007/0167710 A1 | 7/2007 | Unal et al. | |
| 2007/0201736 A1 | 8/2007 | Klingensmith et al. | |
| 2008/0015569 A1 | 1/2008 | Saadat et al. | |
| 2008/0031498 A1 | 2/2008 | Corcoran et al. | |
| 2008/0200815 A1 | 8/2008 | Van Der Steen et al. | |
| 2008/0234582 A1 | 9/2008 | Nair et al. | |
| 2009/0088830 A1 | 4/2009 | Mohamed et al. | |
| 2009/0284332 A1 | 11/2009 | Moore et al. | |
| 2010/0010344 A1 | 1/2010 | Ahn et al. | |
| 2010/0094127 A1 | 4/2010 | Xu | |
| 2010/0174190 A1 | 7/2010 | Hancock et al. | |
| 2010/0312092 A1 | 12/2010 | Listz et al. | |
| 2010/0312109 A1 | 12/2010 | Satoh | |
| 2011/0071404 A1 | 3/2011 | Schmitt et al. | |
| 2011/0160586 A1 | 6/2011 | Li et al. | |
| 2011/0257527 A1 | 10/2011 | Suri | |
| 2012/0065511 A1 | 3/2012 | Jamello, III | |
| 2012/0123271 A1 | 5/2012 | Cai | |
| 2012/0170848 A1 | 7/2012 | Kemp et al. | |
| 2013/0109968 A1 | 5/2013 | Azuma | |
| 2013/0303907 A1 | 11/2013 | Corl | |
| 2013/0303910 A1 | 11/2013 | Hubbard et al. | |
| 2013/0317359 A1 | 11/2013 | Wilson et al. | |
| 2014/0099011 A1 | 4/2014 | Begin | |
| 2014/0100440 A1 | 4/2014 | Cheline et al. | |
| 2014/0180078 A1* | 6/2014 | Nair ..................... A61B 8/5261 600/425 | |
| 2014/0180108 A1* | 6/2014 | Rice ........................ A61B 8/12 600/445 | |
| 2014/0257087 A1 | 9/2014 | Elbasiony et al. | |
| 2014/0268167 A1 | 9/2014 | Friedman et al. | |
| 2014/0276065 A1 | 9/2014 | He | |
| 2014/0316758 A1 | 10/2014 | Yagi et al. | |
| 2014/0350404 A1 | 11/2014 | Nikhil et al. | |
| 2015/0099975 A1 | 4/2015 | Lam et al. | |
| 2015/0141832 A1 | 5/2015 | Yu et al. | |
| 2015/0245776 A1 | 9/2015 | Hirohata et al. | |
| 2015/0356734 A1 | 12/2015 | Ooga et al. | |
| 2016/0007967 A1 | 1/2016 | Johnson et al. | |
| 2017/0193658 A1 | 7/2017 | Cardinal et al. | |
| 2017/0301089 A1 | 10/2017 | Lam et al. | |
| 2017/0330331 A1 | 11/2017 | Bhatt et al. | |
| 2018/0042575 A1 | 2/2018 | Moore et al. | |

FOREIGN PATENT DOCUMENTS

| | | |
|---|---|---|
| EP | 346889 B1 | 1/1995 |
| EP | 851241 A2 | 7/1998 |
| EP | 1387317 A1 | 2/2004 |
| EP | 1609423 A2 | 12/2005 |
| EP | 1988505 A1 | 11/2008 |
| EP | 2488107 A2 | 8/2012 |
| JP | 62221335 A | 9/1987 |
| JP | H09-000522 A | 1/1997 |
| JP | 2001333902 A | 12/2001 |
| JP | 2002530143 A | 9/2002 |
| JP | 2004180784 A | 7/2004 |
| JP | 2006014938 A | 1/2006 |
| JP | 2007029520 A | 2/2007 |
| JP | 2007175542 A | 7/2007 |
| JP | 2007229015 A | 9/2007 |
| JP | 2008508970 A | 3/2008 |
| JP | 2008536638 A | 9/2008 |
| JP | 2009545406 A | 12/2009 |
| JP | 4648652 B2 | 3/2011 |
| JP | 2013507227 A | 3/2013 |
| WO | 0101864 A1 | 1/2001 |
| WO | 2006015877 A1 | 2/2006 |
| WO | 2006113857 A1 | 10/2006 |
| WO | 2006122001 A2 | 11/2006 |
| WO | 2007098209 A2 | 8/2007 |
| WO | 2008016992 A1 | 2/2008 |
| WO | 2008110013 A1 | 9/2008 |
| WO | 2011046903 A2 | 4/2011 |
| WO | 2014186268 A1 | 11/2014 |
| WO | 2017062265 A1 | 4/2017 |
| WO | 2017100274 A1 | 6/2017 |

OTHER PUBLICATIONS

International Patent Application No. PCT/US2016/054588, International Search Report & Written Opinion dated Nov. 30, 2016, 13 pages.

(56) References Cited

OTHER PUBLICATIONS

Dumane et al., "Use of Frequency Diversity and Nakagami Statistics in Ultrasonic Tissue Characterization," IEEE Transactions on Ultrasonics, Ferroelectrics, and Frequency Control, vol. 48, No. 5, Sep. 2001, pp. 1139-1146.
Foster, "Transducer Materials and Probe Construction," Ultrasound in Medicine and Biology, vol. 26, Supp. 1, 2000, pp. S2-S5.
Frijlink et al., "High Frequency Harmonic Imaging in Presence of Intravascular Stents," IEEE Ultrasonics Symposium, 2003, pp. 208-211.
Garcia-Garcia et al., "Imaging of coronary atherosclerosis: intravascular ultrasound," European Heart Journal, vol. 3, 2010, pp. 2456-2469.
Seo et al., "Sidelobe Suppression in Ultrasound Imaging Using Dual Apodization with Cross-Correlation," IEEE Transactions on Ultrasonics, Ferroelectrics, and Frequency Control, vol. 55, No. 10, Oct. 2008, pp. 2198-2210.
Shankar et al., "Computer-Aided Classification of Breast Masses in Ultrasonic B-Scans Using a Multiparameter Approach," IEEE Transactions on Ultrasonics, Ferroelectrics, and Frequency Control, vol. 50, No. 8, Aug. 2003, pp. 1002-1009.
Smith et al., "The Maltese Cross Processor: Speckle Reduction for Circular Transducers," Ultrasonic Imaging, vol. 10, No. 3, Jul. 1988, pp. 153-170.
U.S. Appl. No. 61/218,177, titled Vector Domain Image Enhancement for Mechanically Rotating Imaging Catheters, filed Jun. 18, 2009.
Van Der Steen et al., "IVUS Harmonic Imaging," Ultrasound in Medicine and Biology, vol. 26, Supp. 2, 2000, p. A90.
Wang et al., "Optimizing the Beam Pattern of a Forward-Viewing Ring-Annular Ultrasound Array for Intravascular Imaging," IEEE Transactions on Ultrasonics, Ferroelectrics, and Frequency Control, vol. 49, No. 12, Dec. 2002, pp. 1652-1664.
Waters et al., "Development of a High-Definition Intravascular Ultrasound Imaging System and Catheter," IEEE International Ultrasonics Symposium Proceedings, Oct. 18, 2011, 4 pages.

\* cited by examiner

INTRAVASCULAR ULTRASOUND IMAGING WITH FREQUENCY SELECTIVE IMAGING METHODS AND SYSTEMS

TECHNICAL FIELD

This disclosure relates generally to medical imaging, and more particularly to the use of differential frequency responses of items in medical imaging.

BACKGROUND

Medical imaging techniques generally can be used to collect data and generate in-vivo visualization of anatomical areas of interest. One such example is intravascular imaging, where vascular structures and lumens may be imaged. For instance, intravascular imaging may be used to produce one or more images of the coronary artery lumen, coronary artery wall morphology, and devices, such as stents, at or near the coronary artery wall. Images generated using medical imaging techniques can be useful for diagnostic purposes, such as identifying diagnostically significant characteristics of a vessel.

However, the ability to provide diagnostically significant images in the example of intravascular imaging can be complicated by a variety of factors. For instance, different imaging frequencies may result in varying degrees of contrast, spatial resolution, and apparent brightness of items in an image when displayed. Moreover, image data generated in intravascular imaging may be affected by factors other than imaging frequency, including for example, electrical noise, thermal noise, speckle, and/or relative motion between the vessel and the catheter. All of these noted factors, among others, may significantly affect the quality of the generated image data. For instance, items of diagnostic interest in an imaging view may be difficult to distinguish from other diagnostically insignificant items in the imaging view near the one or more items of interest. Thus, outputting an image where various items in the imaging view are difficult to distinguish from one another may constrain the value of the image for medical diagnostic purposes.

SUMMARY

This disclosure in general relates to using differential frequency response of one or more items within an imaging view to identify the one or more items so as to ultimately produce a diagnostically valuable image. The presently disclosed embodiments may provide an image that includes benefits of high and low frequency imaging (e.g., an image having both high contrast and high spatial resolution) but yet still distinguishes components of interest in the image when presented on a display.

In one example, a plurality of data vectors are acquired at a first frequency and a plurality of data vectors are acquired at a second frequency, where the first frequency is greater than the second frequency. The plurality of first frequency data vectors are formed into a first set of data vectors and the plurality of second frequency data vectors are formed into a second set of data vectors. One or more filters is applied to both the first set of data vectors to form a first modified data set and the second set of data vectors to form a second modified data set. Based on the first modified data set and the second modified data set, a frequency response of one or more items in the imaging view is determined. Using the determined frequency response of one or more items in the imaging view, an image is output on a display.

By applying the one or more filters to the first and second sets of data vectors a more regionalized representation (e.g., as opposed to a more localized representation that is based on an individual pixel basis) of the image data in the first and second sets of data vectors can be produced. This can facilitate direct comparison between the image data in the resulting first and second modified data sets, where such direct comparison may not have otherwise been possible where the first and second sets of data vectors include image data at different frequencies. In addition, applying the one or more filters to the first and second sets of data vectors can be useful for reducing or eliminating artifacts and/or noise from the first and second modified data sets that was originally present in the first and second sets of data vectors.

The effective determination of a frequency response of one or more items in the imaging view can be utilized in a variety of ways to identify specific components and/or regions and output a diagnostically valuable image distinguishing such specific components and/or regions. For example, automatic border detection between two items in the imaging view can be accomplished and incorporated into the output image via a border indicator (e.g., a line delineating an interface between vessel tissue defining a lumen and blood within the lumen). In another example, one or more specific components and/or regions (e.g., blood) can be subtracted out from the output image. Furthermore, in other embodiments specific components and/or regions identified based on differential frequency response at high and low frequencies can be uniquely colorized to distinguish a particular component and/or region. Additionally, a further example may include using differential frequency responses at high and low frequencies of one or more specific components and/or regions to map a characteristic of one modified data set into another modified data set to output an image that sufficiently displays components of interest and suppresses other components as desired for a specific application.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description. Examples of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
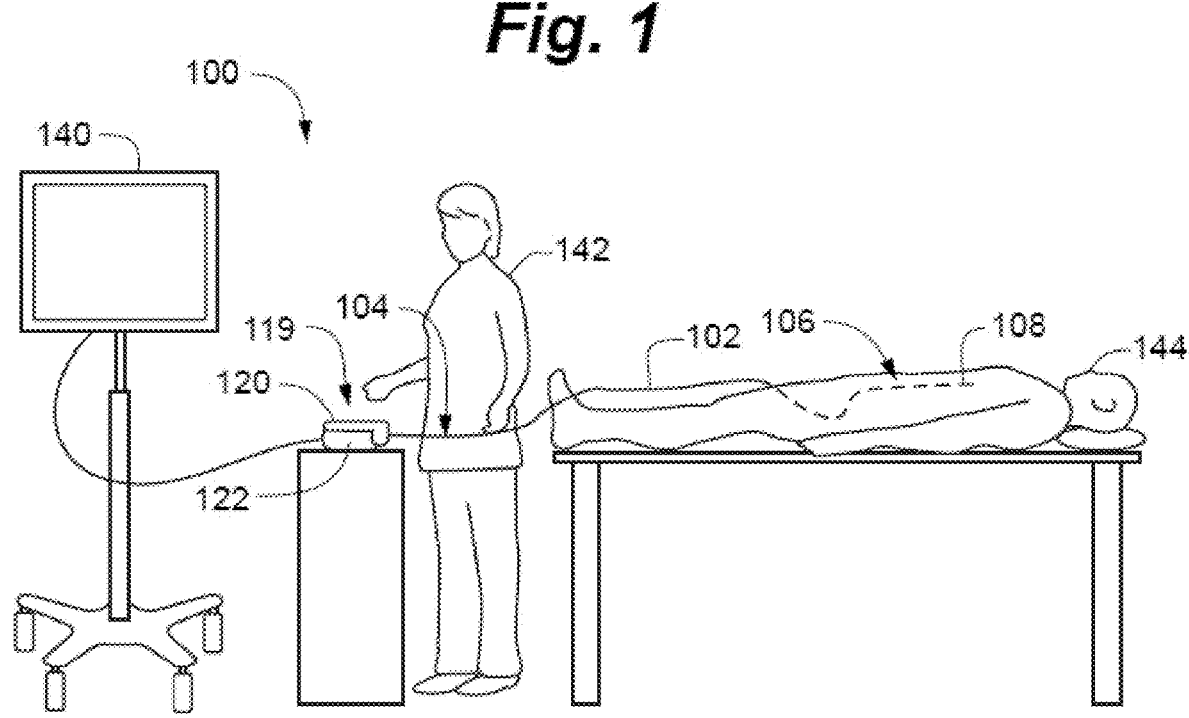
FIG. 1 is an illustrative example of a system configured to perform intravascular imaging.

FIG. 1 illustrates an example of a system 100 that may be configured to perform intravascular imaging. System 100 can include a catheter assembly 102, a translation device 119, and an imaging engine 140. The catheter assembly 102 may include a proximal end 104 and a distal end 106 configured to be inserted into a vessel of a patient 144. In one example, catheter assembly 102 may be inserted into the patient 144 via the femoral artery and guided to an area of interest within the patient 144. The broken lines in FIG. 1 represent portions of catheter assembly 102 within the patient 144.

In some examples, the catheter assembly 102 can include an intravascular imaging device 108 configured to generate imaging data. Intravascular imaging device 108 can be in communication with imaging engine 140. In some embodiments, intravascular imaging device 108 is an ultrasound transducer configured to emit and receive ultrasound energy and generate ultrasound imaging data. In other examples, intravascular imaging device 108 is an optical coherence tomography (OCT) device adapted to emit and receive light and generate OCT data. The image data generated by the imaging device 108 can represent a cross-section of an area of interest within the patient 144 at the location of the imaging device 108. The image data generally will represent a plurality of image items at the cross-sectional location of the imaging device 108, such as, for example, blood, various layers of a vessel of the patient 144, and/or any accumulated matter within the vessel (e.g., plaque).

The translation device 119 can be configured to translate intravascular imaging device 108 of catheter assembly 102. The translation device 119 may comprise a linear translation system (LTS) 122. The LTS 122 may be mechanically engaged with catheter assembly 102 and configured to translate the catheter assembly 102 a controlled distance within the patient 144 during a translation operation, for example a pullback or push-forward operation. System 100 may comprise a patient interface module (PIM) 120 configured to interface the translation device 119 with the catheter assembly 102. Translating the imaging device 108 can allow for cross-sectional image data to be collected at various longitudinal locations within a vessel of the patient 144. This cross-sectional image data at various longitudinal locations can then be compiled, in some applications, to generate a longitudinal cross-sectional image of an area of interest.

The imaging engine 140 can be in communication with intravascular imaging device 108 and translation device 119. According to some examples, the imaging engine 140 may comprise at least one programmable processor. In some examples, the imaging engine 140 may comprise a computing machine including one or more processors configured to receive commands from a system user 142 and/or display data acquired from catheter assembly 102 via a user interface. The computing machine may include computer peripherals (e.g., keyboard, mouse, electronic display) to receive inputs from the system user 142 and output system information and/or signals received from catheter assembly 102 (e.g., rendered images). In some examples, the user interface of the computing machine may be a touchscreen display configured to act as both an input device and an output device. In some examples, imaging engine 140 may include memory modules for storing instructions, or software, executable by the one or more processors.

Figure 2:
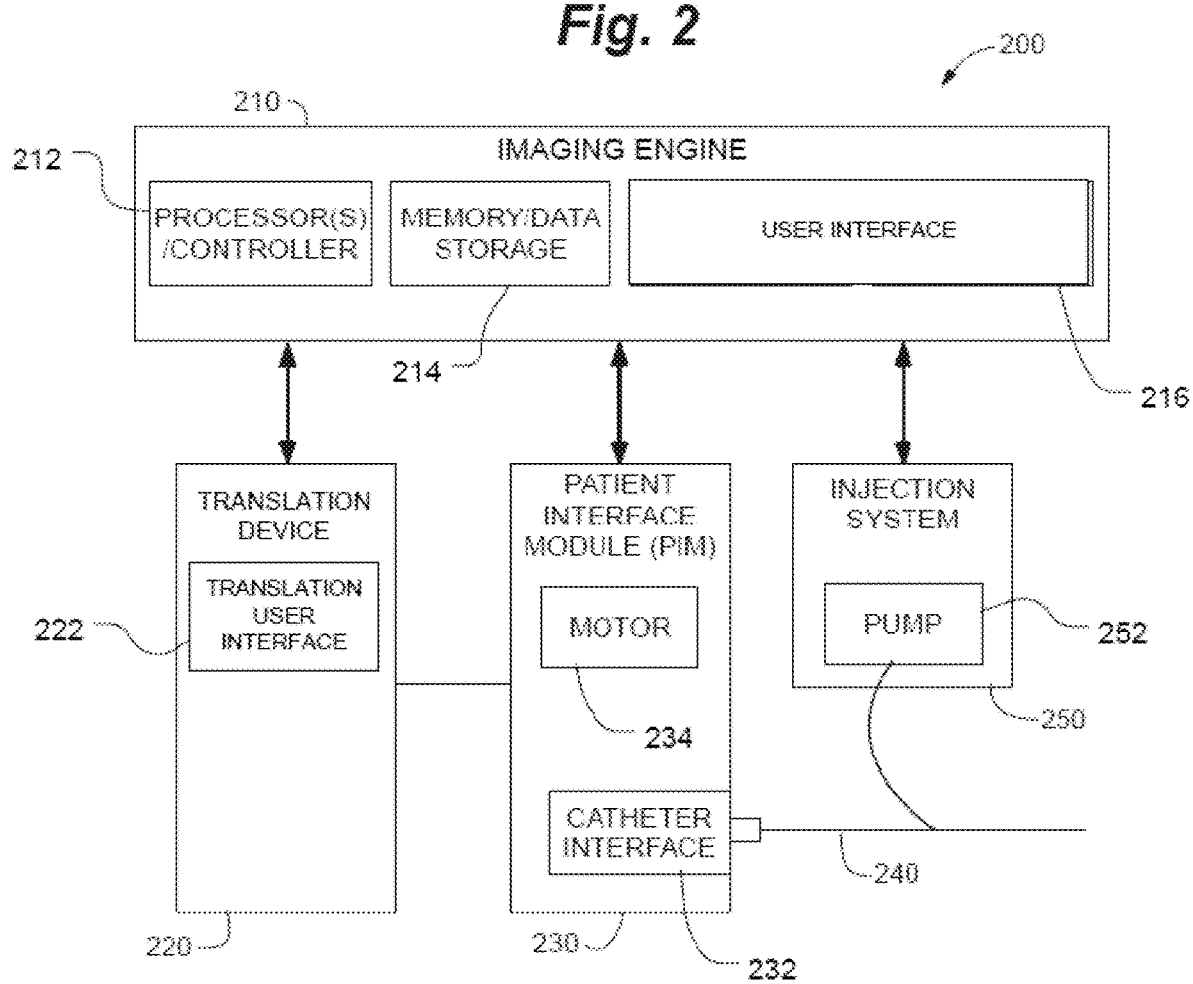
FIG. 2 is a block diagram illustrating a system configured to perform intravascular imaging.

FIG. 2 is a block diagram illustrating system 200 adapted to perform intravascular imaging. System 200 can include PIM 230, translation device 220, injection system 250, catheter assembly 240, and imaging engine 210. System 200 can be configured to be used with an OCT and/or an IVUS based intravascular imaging device.

PIM 230 can provide an electromechanical interface between catheter assembly 240 and imaging engine 210. In some embodiments, PIM 230 may provide a catheter interface 232 to secure catheter assembly 240 to system 200. The PIM 230 may include a motor 234 configured to provide mechanical energy to rotate an intravascular imaging device (e.g., ultrasound transducer) of catheter assembly 240. According to various examples, PIM 230 may provide an electrical interface that transmits signals from the intravascular imaging device of catheter assembly 240 and receives return signals.

Translation device 220 can be configured to provide longitudinal translation of catheter assembly 240. Translation device 220 may comprise a Linear Translation System (LTS). The translation device 220 may be configured to mate with PIM 230 and catheter assembly 240 to enable controlled pullback of an intravascular imaging device of catheter assembly 240. According to some examples, translation device 220 may feature a translation user interface 222 which may comprise a translation display configured to display translation data associated with the translation of the intravascular imaging device to a user of system 200. In some embodiments, translation data may include linear distance traversed and/or translation speed. The translation user interface 222 may be configured to receive inputs from a user to control starting/stopping translation, setting translation speed, resetting linear distance traversed to zero, and/or switching to manual mode. In manual mode, a user may freely move the intravascular imaging device of the catheter assembly forward and backward (e.g., distally and proximally within a vessel). In some examples, the translation device 220 may be configured to enable both pullback and push-forward of the intravascular imaging device at a controlled rate. In another example, the translation device 220 may be configured to oscillate, or cycle, the intravascular imaging device by alternately performing pullback and push-forward operations. In some examples, translation device 220 may include a position sensor configured to measure a distance of a translation operation.

The injection system 250 can be configured to deliver fluid into a vessel of a patient via catheter assembly 240. Although, in some embodiments the system 200 may not include the injection system 250. Injection system 250, when present in the system 200, may comprise an injector pump 252 configured to deliver one or more fluids (e.g., contrast or saline) into the patient. In some examples, the injector pump 252 may be automated, in electrical communication with, and controlled by imaging engine 210. According to some examples, injector pump 252 may comprise a manual pump (e.g., syringe injection) configured to allow a user to manually deliver one or more fluids into the patient. As is discussed elsewhere herein, the injection system 250 may be in fluid communication with an intravascular blood displacement fluid port, which may be associated with catheter assembly 240, such that fluid from the injection system 250 is delivered into a patient's vasculature via the intravascular blood displacement fluid port. As can be appreciated, the injection system 250 may be configured to deliver any number of fluids and any quantity of fluid as appropriate for a specific application of system 200. In some examples, the quantity of blood displacement fluid may comprise a contrast media or saline.

The imaging engine 210, in the illustrated example, includes one or more programmable processors 212, memory/data storage component 214 which can be in communication with the one or more programmable processors 212, and a user interface 216 which can be in communication with the one or more programmable processors 212 and/or the memory/storage component 214. The imaging engine 210 can itself be in communication with the translation device 220, PIM 230, and/or injection system 250 (when present). The user interface 216 can include a display for outputting an image generated based on image data acquired by the catheter assembly 240 (e.g., an ultrasound transducer of the catheter assembly). Before the image is output on the display of the user interface 216, image data acquired by the catheter assembly 240 can undergo one or more image processing techniques at the imaging engine 210. For instance, the memory/data storage component 214 can include instructions, or software, for performing one or more image processing techniques and the one or more processors 212 may execute the image processing techniques based on the instructions.

Figure 3:
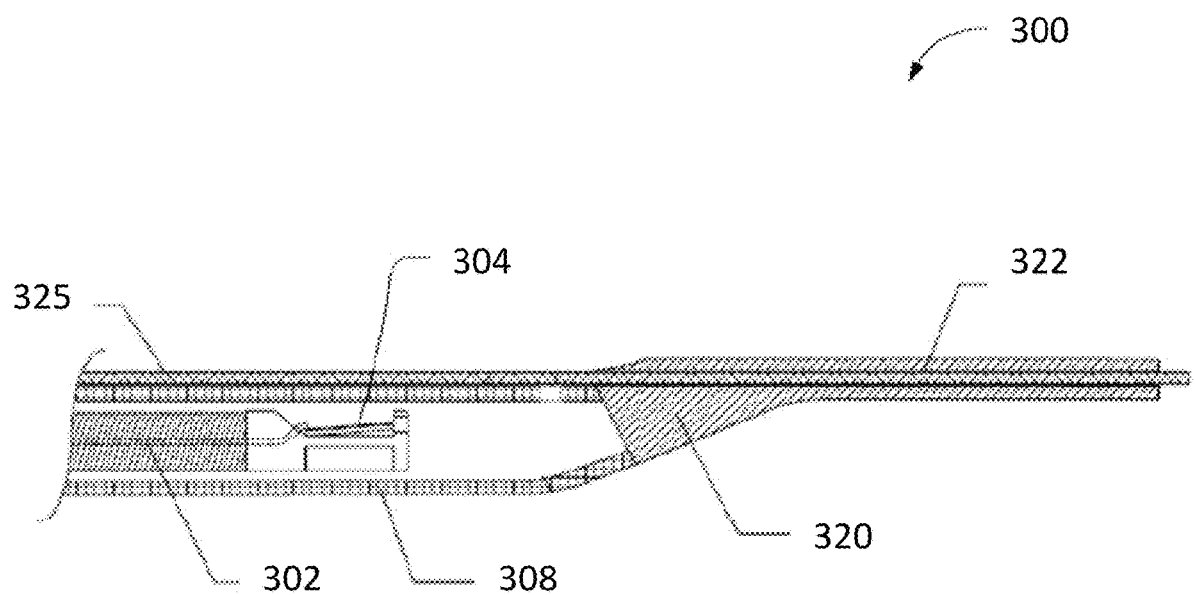
FIG. 3 is a side cross-sectional view of an embodiment of a portion of a catheter assembly.

FIG. 3 shows a side cross-sectional view of an embodiment of a distal portion of a catheter assembly 300, which can be used in the systems described previously with respect to FIGS. 1 and 2. The catheter assembly 300 may include a drive cable 302, a sheath 308, and an ultrasound transducer 304. As noted above, the drive cable may be coupled to a PIM to rotate the drive cable 302 within sheath 308. The ultrasound transducer 304 may be coupled to the drive cable such that the rotation and/or translation of the drive cable causes ultrasound transducer 304 to rotate and/or translate within sheath 308. The ultrasound transducer may be configured to emit and receive acoustic energy during rotation and/or translation to generate ultrasound data. In some examples, the catheter assembly 300 may also include an imaging window (not shown) substantially transparent to the frequency of the acoustic energy emitted by the ultrasound transducer. The catheter assembly 300 may also include a distal end 320 forming a guidewire lumen 322 configured to accept a guidewire 325 to guide the catheter assembly 300 into a vessel of a patient and/or translate the catheter assembly 300 within the vessel.

Figure 4:
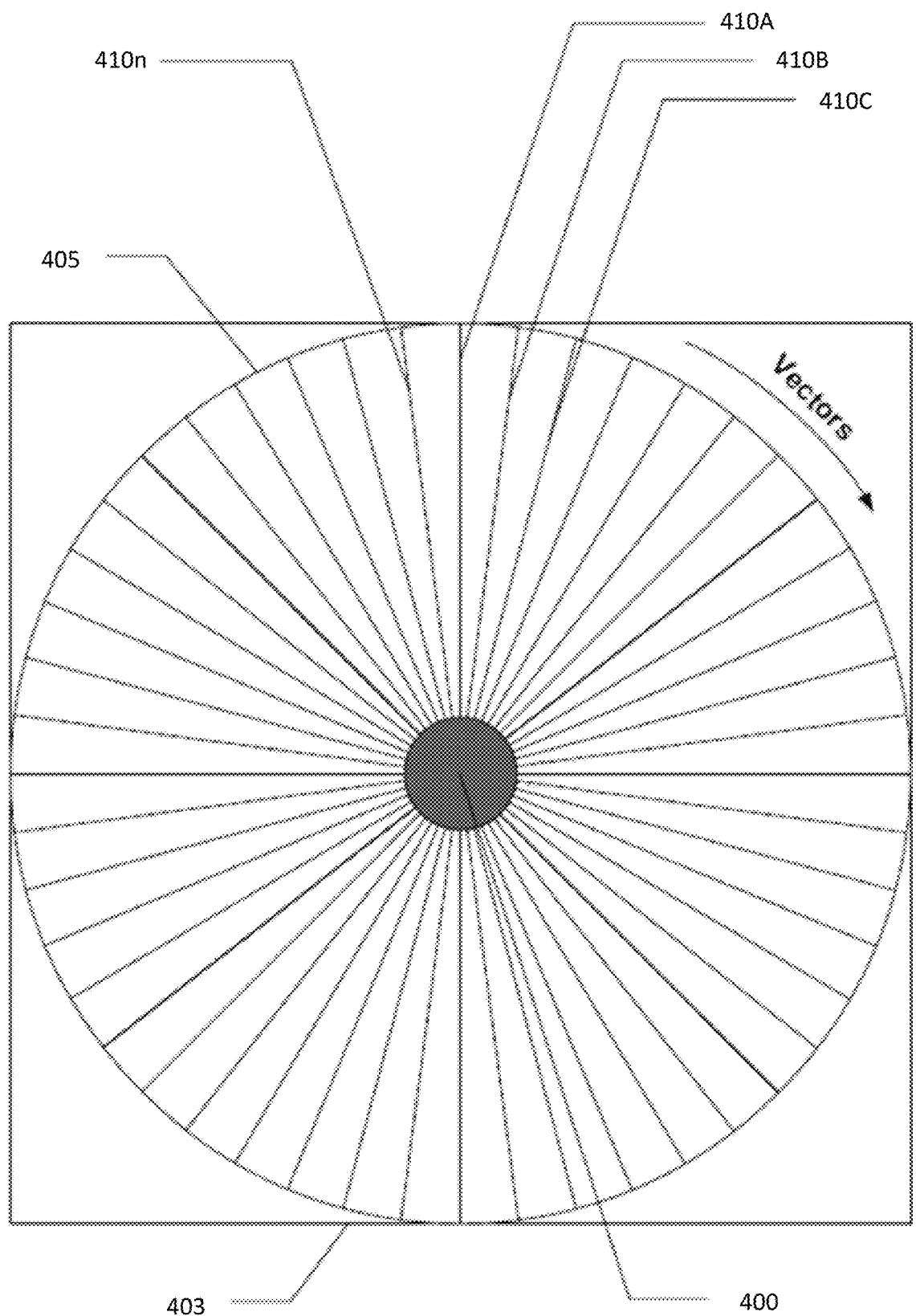
FIG. 4 is a front view of a catheter including data vectors propagated by a transducer of the catheter.

FIG. 4 illustrates a front view of propagating ultrasound data vectors of a catheter 400. In this example, the catheter 400 may be a mechanically rotating ultrasound imaging catheter similar to catheters previously described. Likewise, the catheter 400 may be configured to rotate an ultrasound transducer (not shown) relative to a sheath of catheter 400, and the ultrasound transducer may be configured to generate ultrasound data by emitting and receiving acoustic energy. The ultrasound data vectors illustrated in FIG. 4 are indicative of acoustic energy emitted and received by the ultrasound transducer at different rotational positions. More specifically, each data vector is representative of ultrasound data collected by the ultrasound transducer at different rotational positions of the ultrasound transducer. Each of the data vectors can, in some embodiments, be acquired at different times.

As shown in FIG. 4, the ultrasound transducer of catheter 400 may generate ultrasound data on a vector-by-vector basis as the transducer is rotated. For example, the ultrasound transducer may initially acquire an ultrasound data vector 410A and continue to acquire vectors 410B through 410n as the ultrasound transducer is rotated clockwise. Accordingly, vectors 410A-410n can be representative of a full 360 degree rotation of the ultrasound transducer at a constant longitudinal location. The number of data vectors acquired per rotation may vary depending on the application of the catheter. For instance, in some embodiments, the IVUS catheter is configured to generate between about 500 and about 5000 vectors per rotation. For example, in an embodiment generating 512 vectors per rotation the angle between data vectors may then be characterized as approximately $2\pi/512$ radians or 360/512 degrees. In an example of a catheter configured to generate 4096 vectors per rotation, the angle between data vectors may be approximately $2\pi/4096$ or 360/4096 degrees. FIG. 4 also provides a representation of a data frame 403 that comprises vectors 410A-410n. Data frame 403 includes vectors emitted and received at a same longitudinal location of the ultrasound transducer. A field of view 405 of the catheter 400 may be based on the magnitude of the data vectors propagated by the catheter and may vary to suit a specific application. The magnitude of the data vectors may be based on a number of factors, for example, the frequency of the emitted pressure wave and/or the power level of the pressure wave.

In some embodiments, the ultrasound transducer of catheter 400 can emit acoustic energy at a first frequency and receive a backscatter of the acoustic energy to acquire an ultrasound data vector at the first frequency. In addition, the ultrasound transducer may emit acoustic energy at a second frequency, different from the first frequency (e.g., the first frequency can be greater than the second frequency), and receive a backscatter of the acoustic energy to acquire another ultrasound data vector, this time at the second frequency. As the ultrasound transducer rotates at a constant longitudinal position, additional ultrasound data vectors can be acquired at the first frequency and the second frequency. For example, in one embodiment, the ultrasound transducer can emit acoustic energy at the first frequency to acquire first frequency data vector 410A. At a subsequent time, the ultrasound transducer can rotate at a same longitudinal location and emit acoustic energy at the second frequency to acquire second frequency data vector 410B. The ultrasound transducer can continue to rotate through 360 degrees at the longitudinal location alternating (whether consecutively or non-consecutively) between the first frequency and the second frequency to acquire a plurality of first frequency data vectors and second frequency data vectors. In this way, the acquired plurality of first and second frequency data vectors are distributed circumferentially around the same longitudinal location of the ultrasound transducer such that adjacent data vectors (e.g., 410A, 410B) may alternate to comprise ultrasound data at the different first and the second frequencies. In one application, the first frequency can be, for example, approximately 60 MHz while the second frequency can be approximately 40 MHz. In some examples, a different number of high frequency data vectors can be obtained as compared to low frequency data vectors (e.g., more high frequency data vectors can be obtained than low frequency data vectors).

One advantage to acquiring data vectors at both a high frequency (e.g., the first frequency) and low frequency (e.g., the second frequency) is the ability to generate an image having both high contrast and high spatial resolution. Image data acquired at a low frequency (e.g., equal to or less than 40 Mhz) generally exhibits good contrast but poor spatial resolution, while image data acquired at a high frequency (e.g., greater than 40 MHz) generally exhibits good spatial resolution but poor contrast. Thus, by acquiring data vectors (e.g., adjacent data vectors) at a high and low frequency an image may be generated that exhibits both high contrast and spatial resolution.

Figure 5:
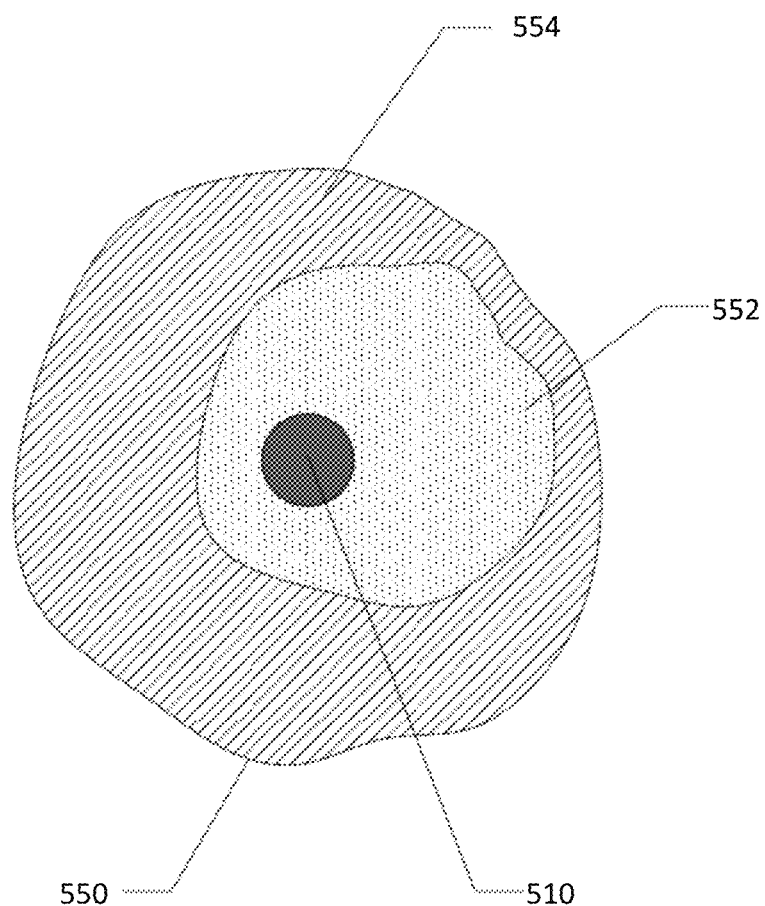
FIG. 5 is a cross-sectional view of a catheter in a vessel lumen.

FIG. 5 is a cross-sectional view showing a catheter 510 within a vessel 550. As noted above, catheter 510 may be directly guided into the vessel or, in certain examples, be guided into the vessel via a guide wire. Vessel 550 may be a vessel of a vascular system of a patient including a vessel wall 554 defining a vessel lumen 552 through which blood flows. In addition to blood, the vessel lumen 552 may also include, in various applications, one or more plaque components that have accumulated within the vessel lumen 552 over time. Such plaque components can include, for instance, atherosclerotic plaque such as lipids.

Figure 6:
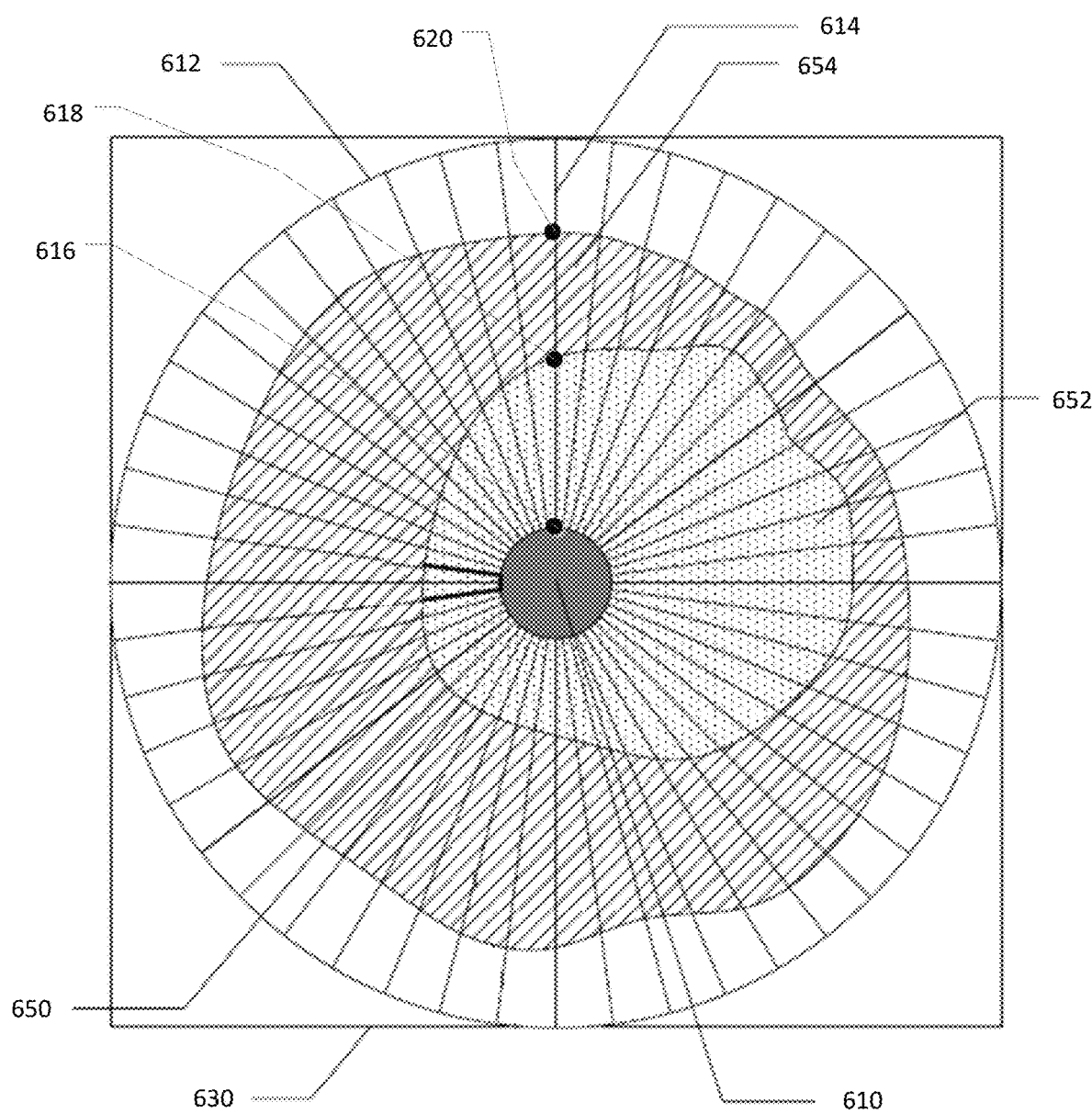
FIG. 6 is a cross-sectional view of a catheter in a vessel lumen including data vectors propagated by the catheter.

FIG. 6 shows a cross-sectional view of a catheter 610 within a vessel 650 and an overlay of ultrasound data vectors propagated by the catheter 610. Vessel 650 is similar to the vessel described previously with respect to FIG. 5 and catheter 610 is similar to the catheters described previously. As in those examples, catheter 610 may include an ultrasound transducer configured to generate ultrasound data in the form of a plurality of data vectors. In this example, each data vector corresponds to ultrasound data collected by emitting acoustic energy and receiving a reflection of the energy, or backscatter, from vessel 650 and/or items of or within vessel 650. Different portions of the vessel, for example vessel wall 654 as well as fluid (e.g. blood) and plaque in vessel lumen 652, are likely to have different material compositions. The different material compositions of the different portions of the vessel can result in different responses to the emitted acoustic energy. The different responses of the various portions can be exploited in many embodiments to distinguish different portions, or regions of interest, of the vessel and in turn provide a more diagnostically valuable image.

For instance, variations in ultrasound backscatter levels along a data vector may be used to determine the boundary between the lumen and the wall of a vessel. For example, vessel wall 654 and the fluid within vessel lumen 652 (e.g., blood) may reflect varying amounts of acoustic energy emitted by the ultrasound transducer of catheter 610. Accordingly, the ultrasound data collected along a data vector may capture the variation in the ultrasound backscatter level between vessel wall 654 and vessel lumen 652. For example, a first region of data vector 614 between data points 616 and 618 may have a backscatter level consistent with blood flowing within the vessel lumen while a second region of data vector 614 between data points 618 and 620 may have a backscatter level consistent with vessel wall 654. Further, the transition between the backscatter levels of the first region and the second region may be used to identify the boundary between vessel wall 654 and vessel lumen 652, located approximately at data point 618. As noted above, data frame 630 may comprise data vectors acquired during a full 360 degree rotation of the ultrasound transducer of catheter 610 (e.g., at a constant longitudinal position of the ultrasound transducer within the vessel lumen 652).

In addition to using variations in ultrasound backscatter levels along a single data vector, variations in backscatter of distinct data vectors (e.g., adjacent data vectors) can also be used to exploit different responses of different portions of the vessel. In particular, different portions of the vessel can have different rates of change in a backscatter property as a function of frequency. For example, blood has a dynamic response to changes in frequency such that as frequency is increased blood exhibits a relatively large increase in backscatter. On the other hand, other items in an imaging view (e.g., tissues and plaque, such as lipids) may have relatively more stable responses to changes in frequency such that as frequency is increased these items exhibit a relatively small change (e.g., increase or decrease) in backscatter as a function of frequency.

The different response of various portions of the vessel (e.g., blood versus tissues and plaque) to changes in frequency has traditionally created problems in generating a diagnostically valuable intravascular image. As described previously, it may be beneficial to acquire data vectors at both a high frequency and a low frequency in order to generate an image having both high contrast and high spatial resolution. However, as noted, different portions of the vessel can have different rates of change in a backscatter property as a function of frequency. In general, a backscatter property of a particular portion of the vessel 650 (e.g., tissue, blood, plaque) relates to the apparent brightness of the particular portion in an intravascular image. Therefore, the more dynamic an item's response is to changes in frequency, the brighter that item will appear in the image as frequency is increased. For example, an increase in frequency can result in a significant increase in the apparent brightness of blood in an intravascular image due to blood's relatively large increase in backscatter with increases in frequency. This can result in raising the brightness of blood within the vessel to an average brightness equal to or greater than plaque and/or tissue surrounding the blood. Consequently, it can be difficult to distinguish blood within the vessel lumen from plaque and/or tissue in the resulting intravascular image.

Figure 7:
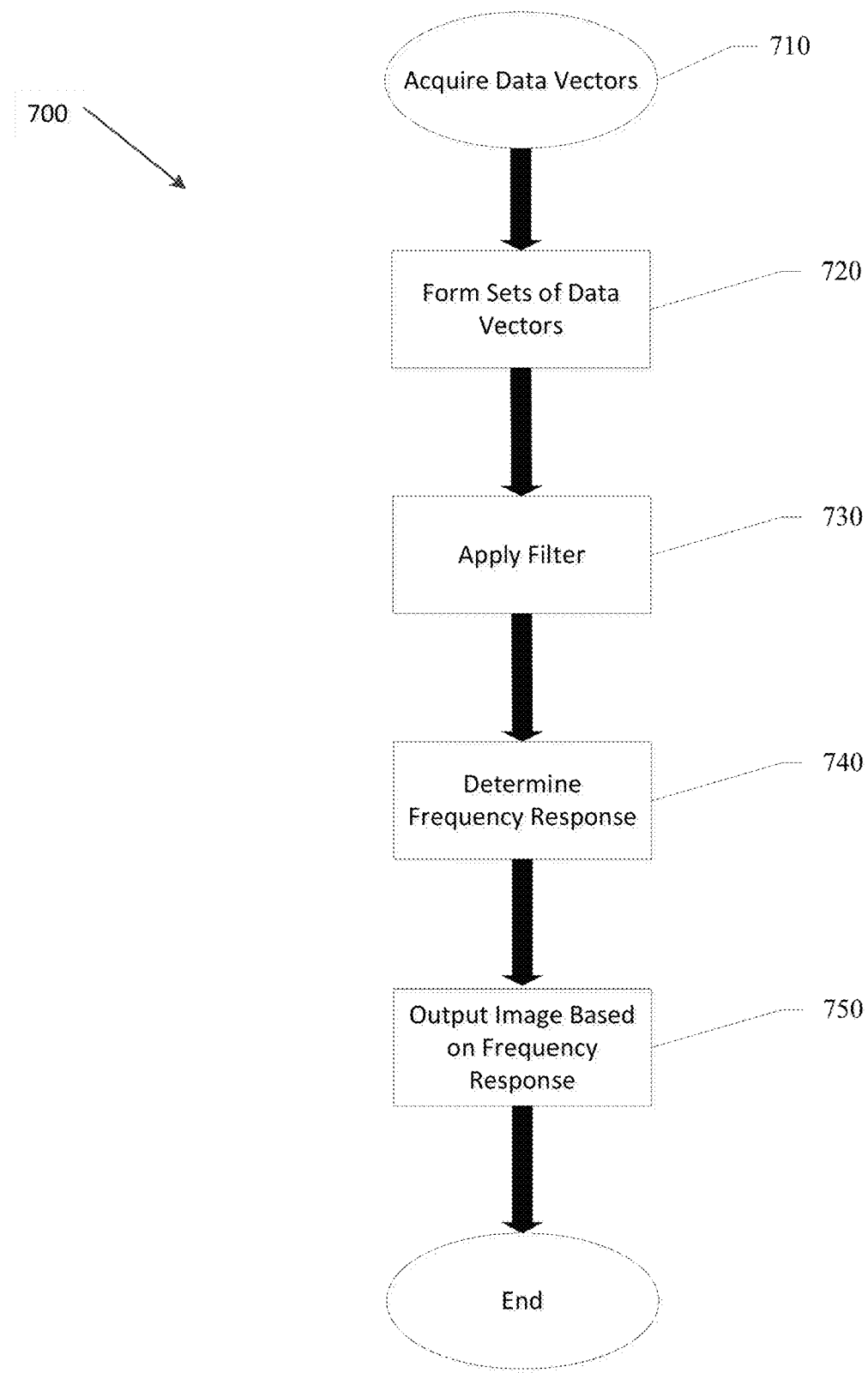
FIG. 7 is a flow diagram illustrating a method for generating an image using frequency responses of one or more items in an imaging view.

However, variations in backscatter of distinct data vectors (e.g., adjacent data vectors) as a function of frequency can used to exploit the different responses of different portions of the vessel in order to distinguish these different portions of the vessel in a generated image. FIG. 7 illustrates one example of a flow diagram of a method 700 for generating an image using differential frequency responses of one or more items in an imaging view. The method 700, in using differential frequency responses of one or more items in an imaging view, can help distinguish various items in a vessel from one another (e.g., discerning blood v. plaque), and as a result output a diagnostically valuable image. The method 700 will be discussed throughout the remainder of the present description and in conjunction with the description of FIGS. 7 and 8.

In the embodiment of FIG. 7, the method 700 includes initially acquiring data vectors in step 710. Data vectors can be acquired in some examples using an intravascular imaging system having an intravascular imaging device (e.g., ultrasound transducer) for emitting and receiving acoustic energy at the imaging device similar to that described previously (e.g., with respect to FIG. 4). In one embodiment, an ultrasound transducer can emit acoustic energy at a first frequency to acquire a first frequency data vector representing one or more items in an imaging view. For example, the first frequency can be a high frequency of approximately 60 MHz. At a subsequent time, the ultrasound transducer can rotate at a same longitudinal location within a vessel and emit acoustic energy at a second frequency to acquire a second frequency data vector representing one or more items in an imaging view. The second frequency can be, for instance, a low frequency of approximately 40 MHz, such that the first frequency is greater than the second frequency. The first and second frequencies may include any frequencies for exploiting differences in frequency response among tissues. Moreover, the first frequency data vector and the second frequency data vector can be adjacent data vectors such that the first and second data vectors provide ultrasound data pertaining to a substantially same portion of the vessel. In the described embodiment, the ultrasound transducer can continue to rotate through 360 degrees at the longitudinal location alternately emitting temporally separate acoustic energy at the first frequency and the second frequency to acquire a plurality of first frequency data vectors and a plurality of second frequency data vectors. In this way, the acquired plurality of first and second frequency data vectors are distributed circumferentially around the same longitudinal location (e.g., within a single frame) of the ultrasound transducer such that circumferentially adjacent data vectors alternate to comprise ultrasound data at the first frequency and the second frequency. As noted previously, in some examples a different number of high frequency and low frequency data vectors can be acquired, such as a greater number of high frequency data vectors than low frequency data vectors (e.g., by a factor of two-to-one, by a factor of three-to-one, etc.).

Once the data vectors have been acquired in step 710, sets of data vectors can be formed in step 720. In one example, a first set of data vectors can be formed using one or more of the plurality of first frequency data vectors and a second set of data vectors can be formed using one or more of the second frequency data vectors. In such an example, the first set of data vectors include ultrasound data at the first (e.g., higher) frequency, while the second set of data vectors include ultrasound data at the second (e.g., lower) frequency. In one application, the imaging engine, and in particular a processor of the imaging engine, can be configured to form the first and second sets of data vectors. A number of data vectors in each of the first and second sets of data vectors need not be the same. As an example, the first set of data vectors at the higher frequency can include a number of data vectors that is greater than a number of data vectors in the second set of data vectors at the lower frequency. For instance, the first set of data vectors at the higher frequency can have two, three, four, etc. high frequency data vectors for every one low frequency data vector in the second set of data vectors at the lower frequency.

The formed sets of data vectors can each undergo one or more image processing techniques. In the embodiment of the method 700, the image processing technique includes applying a filter in step 730. For instance, a first filter can be applied to the first set of data vectors and a second filter can be applied to the second set of data vectors, where the first and second filters are the same in some embodiments and/or where the first and second filters are different in some embodiments. At least one filter applied in the exemplary method 700 can include, for instance, any process that results in a decrease in a degree of detail represented by a set of data vectors (e.g., to produce a more regionalized representation in such set of data vectors). As an example, the step 730 can include application of a smoothing filter to both the first set of data vectors and the second set of data vectors. The smoothing filter can be a Gaussian blur or other appropriate smoothing filter. In some further examples, the step 730 can additionally include applying a sharpening filter after the smoothing filter to one or both of the first and second sets of data vectors. The sharpening filter, for instance when applied after the smoothing filter (which can act to decrease detail as described above), can be configured to clarify detail represented by a set of data vectors. For example, the smoothing filter can enhance detail of any or all portions of image data represented by the first and/or second sets of data vectors (e.g., one or more edges and one or more portions encompassed within the one or more edges). Application of the sharpening filter in such examples can include generating a Laplacian pyramid for the one or both sets of data vectors to which the sharpening filter is applied. Other filters in addition to, or as an alternative to, smoothing and sharpening filters may also be utilized. Applying the filter in step 730 to a set of data vectors can produce a more regionalized representation (e.g., as opposed to a more localized representation that is based on an individual pixel basis) of the image data in such set of data vectors. As a result, applying the filter to a set of data vectors can be useful for reducing or eliminating artifacts and/or noise present in the original set of data vectors.

In the embodiment of the method 700, the filter may be applied to the first set of data vectors to produce a first modified data set such that the first modified data set can include image data that is more regionalized relative to the first set of data vectors. In addition, the filter may be applied to the second set of data vectors to produce a second modified data set such that the second modified data set can include image data that is more regionalized relative to the second set of data vectors. In addition to reducing or eliminating artifacts and/or noise, applying the filter to the first and second sets of data vectors, where the first and second sets include data vectors at high and low frequencies respectively, can facilitate direct comparison between the resulting first and second modified data sets. Accordingly, in this embodiment the filtering step is done before the comparison step.

In some embodiments, the filter can include any filter useful for creating regionalized data. In one embodiment, the filter can be a smoothing filter applied to the first and second sets of data vectors as a Gaussian blur. Thus, a Gaussian blur filter can be applied to the first set of data vectors to form the first modified data set, as well as to the second set of data vectors to form the second modified data set. A Gaussian blur acts to smooth an image using a Gaussian function. In some applications, the Gaussian blur can be applied as a large kernel-size blur. In other embodiments, the first and second data vectors can be blurred using other non-Gaussian functions. In another embodiment, the filter applied to the first and second sets of data vectors can be a high pass, low pass, or other temporal filter.

Figure 8:
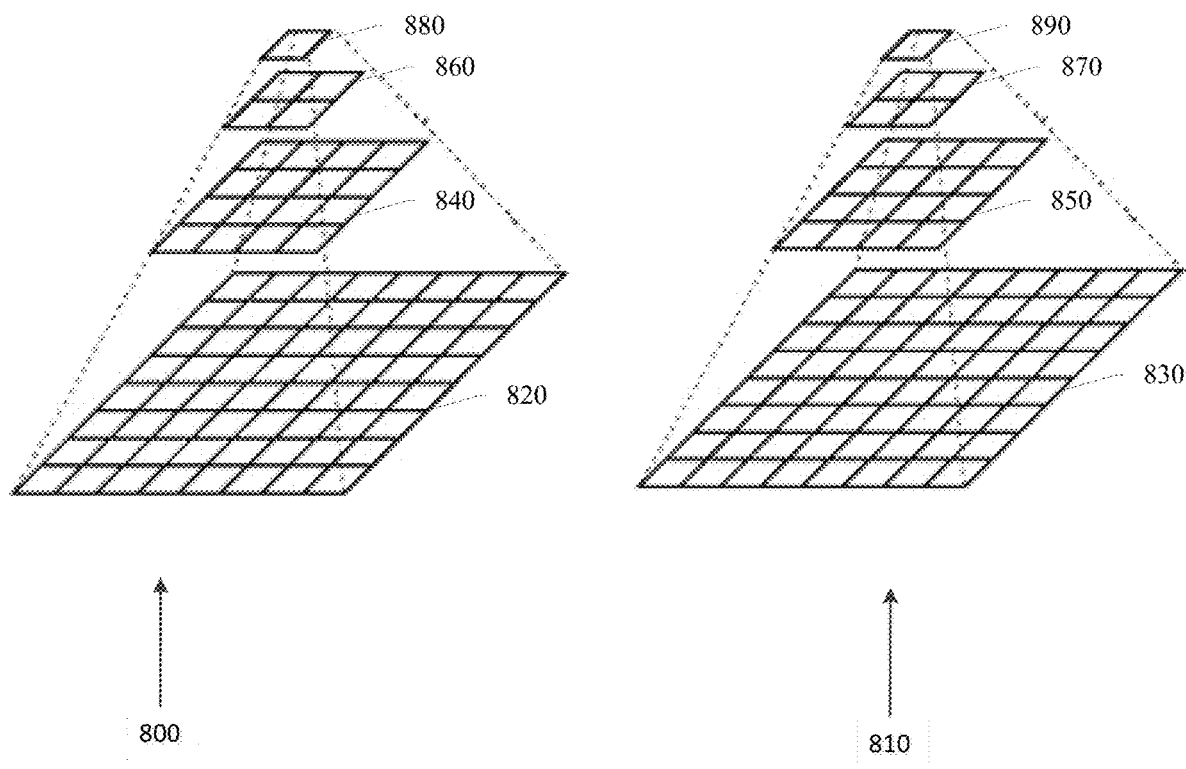
FIG. 8 is a schematic illustration of two image pyramids constructed using a first set of data vectors and a second set of data vectors, respectively.

In further examples, where the filter is a smoothing filter, applying the filter to each of the first and second sets of data vectors can include repeated smoothing so as to construct a pyramid representation of both the first and second sets of data vectors. FIG. 8 shows a schematic illustration of two image pyramids 800 and 810. The first image pyramid 800 is constructed using the first set of data vectors at the first frequency, while the second image pyramid 810 is constructed using the second set of data vectors at the second frequency. Thus, a first level 820 of the first pyramid 800 includes an image based on the first set of data vectors, while a first level 830 of the second pyramid 810 includes an image based on the second set of data vectors. Because the first set of data vectors are at a first high frequency and the second set of data vectors are at a second low frequency, the first and second sets of data vectors may not be directly comparable.

In the present example, the pyramids 800 and 810 are both constructed using a Gaussian blur as a smoothing filter such that the pyramids 800 and 810 are Gaussian pyramids. A second level 840 of the first pyramid 800 is created by applying the Gaussian blur to the first level 820 (e.g., the image based on the first set of data vectors), resulting in the first level 820 having a greater resolution than a resolution of the second level 840 (as shown schematically by the decrease in pixels from the first level 820 to the second level 840). Similarly, a second level 850 of the second pyramid 810 is created is created by applying the Gaussian blur to the first level 830 (e.g., the image based on the second set of data vectors), resulting in the first level 830 having a greater resolution than a resolution of the second level 850. As such, the second levels 840, 850 include data that is more regionalized relative to the respective first levels 820, 830. This process may be repeated for subsequent levels 860, 880 (up to n many levels) of the first pyramid 800, where each subsequent level is a result of smoothing performed on the immediately previous level. The process may also be repeated for subsequent levels 870, 890 (up to n many levels) of the second pyramid 810, where each subsequent level is a result of smoothing performed on the immediately previous level. Any scale factor between levels can be used. In the illustrated example, the scale factor between levels of both pyramids 800 and 810 is two, but in other examples various scale factors can be used as suited for a particular application. For instance, the scale factor may be selected based on the degree to which noise and/or artifacts are present (or expected to be present) in the first and second sets of data vectors. Furthermore, any number of levels can be included in the pyramids 800 and 810, and in many cases it will be beneficial to generate a same number of levels for both pyramids 800 and 810.

In some embodiments, the first modified data set can include a level of the first pyramid 800 above the lowest level (e.g., the highest level). Further, the second modified data set can include a level of the second pyramid 810 above the lowest level (e.g., the highest level). In other embodiments, further processing can be performed using both the first and second pyramids. For example, a first Laplacian pyramid can be constructed based on the first pyramid 800, and a second Laplacian pyramid can be constructed based on the second pyramid 810. Each of the first and second Laplacian pyramids may be constructed by taking a difference between an up-sampled level (e.g., level 840 or 850, respectively) and a previous level (e.g., level 820 or 830, respectively) and using this difference as a corresponding level in the respective first and second Laplacian pyramids. In such embodiments, the first modified data set can include a level of the first constructed Laplacian pyramid and the second modified data set can include a level of the second constructed Laplacian pyramid.

Returning to the embodiment of the method 700 shown in FIG. 7, after the filter has been applied to both the first set of data vectors to form the first modified data set and the second set of data vectors to form the second modified data set in step 730, a frequency response can be determined in step 740. The frequency response of one or more items in the imaging view (e.g., blood, tissue, plaque) can be determined based on the first modified data set and the second modified data set. In particular, a comparison between the first modified data set and the second modified data set can be used to determine a frequency response of one or more items in the imaging view. By determining a frequency response of one or more items in the imaging view based on the first and second modified data sets, not only is a direct comparison possible but detrimental effects caused by artifacts and/or noise present in the original first and second sets of data vectors can be reduced or eliminated due to the regionalized nature of the data included in the first and second modified data sets.

In one example of determining a frequency response of one or more items in the imaging view, a difference between the first modified data set (e.g., high frequency data to which the filter has been applied) and the second modified data set (e.g., low frequency data to which the filter has been applied) can be calculated. Calculating the difference between the first modified data set and the second modified data set can provide an indication of regions and/or items that exhibit an increase in response at a higher frequency (e.g., blood). In addition, in some examples, a difference between the second modified data set and the first modified data set can be calculated to provide an indication of regions and/or items that exhibit a decrease in response at a higher frequency. The extent to which an item and/or region exhibits a change in response as a function of frequency can be used to identify specific items and/or regions of a vessel.

In step 750, an intravascular image can be created based on a differential frequency response determined in step 740. Differential frequency responses of one or more items and/or regions in an imaging view can be used to output an image that visually distinguishes various items and/or regions of the vessel, thus providing a diagnostically valuable image. Visually distinguishing various items and/or regions of the vessel on the output image can be accomplished in a multitude of ways.

In a first example, where applying the filter includes constructing first and second Laplacian pyramids, an image may be outputted that is constructed based on the first and second Laplacian pyramids. In particular, the outputted image can be constructed using data from both the first and second Laplacian pyramids. In an exemplary embodiment, an algorithm may be used to map desired characteristics from both the first and second Laplacian pyramids into a composite pyramid, where the composite pyramid is collapsed to form the output image. In such embodiment, when building the composite pyramid, each particular level of the composite pyramid is constructed using data from either a same corresponding level or a lower resolution level of the first and second Laplacian pyramids. Thus, the composite pyramid in the described embodiment is constructed without using image data from the highest resolution level of the first and second Laplacian pyramids. Doing so may help to prevent noise and/or artifacts in the highest resolution level of the first and second Laplacian pyramids from detrimentally affecting use of the composite Laplacian pyramid. In determining which of the first and second Laplacian pyramids to pull information from when constructing a particular level of the composite pyramid, parameters and/or an algorithm may be employed to target desired characteristics of the first and second Laplacian pyramids for inclusion in the composite pyramid. Such parameters and algorithm can be implemented to, for instance, compare corresponding data in the first and second Laplacian pyramids to discern a change in response of an item or region of a vessel to an increase in frequency. Depending on the desired application, the result of this comparison can be used to decide which of the first and second Laplacian pyramids to pull data from.

For example, in one application (e.g., ultrasound imaging of arterial disease) an algorithm can be utilized to map desired characteristics from both the first and second Laplacian pyramids into a composite pyramid by applying preferential weighting. In such an example, the first Laplacian pyramid may be calculated from images acquired at a higher frequency (e.g., 60 MHz) and the second Laplacian pyramid may be calculated from images acquired at a lower frequency (e.g., 40 MHz). The composite pyramid may be calculated by weighting one or more levels of the first high frequency Laplacian pyramid and the second low frequency Laplacian pyramid.

One particular example can involve preferentially weighting the first level of the first high frequency (e.g., 60 MHz) Laplacian pyramid, which may provide better spatial resolution, while preferentially weighting the second level of the second low frequency (e.g., 40 MHz) Laplacian pyramid, which may provide better contrast (e.g., tissue contrast). For illustrative purposes, in the present example the preferential weighting used is 75% to the level in a pyramid given preference (e.g., first level in first pyramid) and 25% to the corresponding level in a pyramid that is not given preference (e.g., first level in second pyramid). This can be repeated for multiple corresponding levels of the pyramids, where the pyramid having the level receiving the preferential weighting can vary on a level-by-level basis. Although preferential weighting of 75% is described here, in other examples the preferential weighting applied to a level in a pyramid given preference can be any weight over 50%, and the specific weight chose can vary based on a desired application. After applying preferential weighting to the first level of the first high frequency Laplacian pyramid and the second level of the second low frequency Laplacian pyramid, the composite pyramid can be formed to have a first level as the sum of (a) 0.75 times the first level of the first high frequency Laplacian pyramid and (b) 0.25 times the first level of the second low frequency Laplacian pyramid. Also, the composite pyramid can be formed to have a second level as the sum of (a) 0.25 times the second level of the first high frequency Laplacian pyramid and (b) 0.75 times the second level of the second low frequency Laplacian pyramid. An output image may then be formed by combining the described first and second levels of the composite pyramid. Similar preferential weighting can be used for additional corresponding levels (e.g., a third level) of first high frequency pyramids and second low frequency pyramids.

In other embodiments, the composite pyramid may be formed by other combination techniques in conjunction with, or as an alternative to, preferential weighting. For instance, a level of the composite pyramid may be calculated by comparing corresponding levels of the first high frequency and second low frequency Laplacian pyramids. Comparison operations can include determining a function value (e.g., a minimum value, a maximum value, a median value, a mean value) for a particular level. Utilization of a comparison operation can serve, for instance, to utilize image data having less detrimental noise. Other techniques may include combining one or more comparison operations with preferential weighting that may vary with imaging frequency. In many cases, comparison operations can function similar to preferential weighting, as the use of a minimum of maximum through comparison can function to preferentially weight data based on that minimum or maximum.

One example of a technique that can be utilized by an algorithm to combine comparison operations with preferential weighting to output an image is described here. This example utilizes a first high frequency (e.g., 60 MHz) Gaussian pyramid, a second low frequency (e.g., 33 MHz) Gaussian pyramid, a first high (e.g., 60 MHz) frequency Laplacian pyramid, and a second low frequency (e.g., 33 MHz) Laplacian pyramid, with each said pyramid having four corresponding levels. A first value (1) is calculated by preferentially weighting a fourth level of the second low frequency Gaussian pyramid and obtaining a difference between the preferentially weighted fourth level of the second low frequency Gaussian pyramid and a fourth level of the first high frequency Gaussian pyramid. A second value (2) is calculated by taking a function value (e.g., a minimum value) across corresponding fourth levels of the first high frequency and second low frequency Laplacian pyramids. A third value (3) is calculated by taking a function value (e.g., a minimum value) across corresponding third levels of the first high frequency and second low frequency Laplacian pyramids. A fourth value (4) is calculated by taking a function value (e.g., a minimum value) across corresponding second levels of the first high frequency and second low frequency Laplacian pyramids. A fifth value (5) is calculated by taking a function value (e.g., a minimum value) across corresponding first levels of the first high frequency and second low frequency Laplacian pyramids. After calculating the second (2), third (3), fourth (4), and fifth (5) values, each of the second (2), third (3), fourth (4), and fifth (5) values may or may not be preferentially weighted based on the application. As one example, the second (2), third (3), fourth (4) values are given a same weight, while the fifth (5) value is given less weight. A sixth value (6) is calculated to maintain spatial resolution of the first high frequency Laplacian pyramid by applying a weighting less than one to the first level of the first high frequency Laplacian pyramid. The calculated of values (1), (2), (3), (4), (5), and (6) can then be added together to calculate an image to be output. Thus, in this example weighting factors and comparison across corresponding pyramid levels (e.g., for a minimum value) is used to calculate an image to be output.

Moving to another example for visually distinguishing various items and/or regions of the vessel on the output image, an image may be created (e.g., on an image display region of the user interface) with a significantly reduced appearance of a blood field by substantially subtracting out the blood field from the output image. For instance, an intensity output for each pixel on the display can be applied by multiplying (1) regions exhibiting an increase in response at the higher frequency (determined e.g., by taking a difference between the first modified data set (including high frequency data to which the filter has been applied) and the second modified data set (including low frequency data to which the filter has been applied)) by (2) a weighting factor to obtain a product. The weighting factor can be a constant number, which may be selected depending on the application and desired characteristics of the image to be output. This product can then be subtracted from the first set of data vectors (including unmodified high frequency data). This results in an image where items and/or regions exhibiting an increase in response at the higher frequency, such as blood, are displayed with a reduced appearance (e.g. reduced brightness) and/or eliminated from the image entirely. The weighting factor can be selected based on whether it is desired in a specific application to merely reduce the appearance of items and/or regions exhibiting an increase in response at the higher frequency or rather to eliminate such items and/or regions. As one example, the use of a weighting factor can enable modifying an image brightness of one or more image features of interest, such as reducing an image brightness of a blood filed in a lumen.

In another example of outputting an image based on differential frequency response, a blood field can be colorized to distinguish the blood field from other items and/or areas of the vessel. In the present example, a three color output of red, green, and blue will be used for illustrative purposes, but in various embodiments any number of various colors can be used. For instance, in one application the blood field as displayed on the output image may be colored red to distinguish the blood field. To accomplish this, a green and blue value of a red-green-blue output is calculated by multiplying (1) regions exhibiting an increase in response at the higher frequency (determined e.g., by taking a difference between the first modified data set (including high frequency data to which the filter has been applied) and the second modified data set (including low frequency data to which the filter has been applied)) by (2) a weighting factor to obtain a product. This product can then be subtracted from the first set of data vectors (including unmodified high frequency data), and the result is used as the calculated green and blue value of the red-green-blue output. The red value of the red-green-blue output is represented by the first set of high frequency data vectors. The result is an output image where the blood field is colorized red to distinguish it from other items and/or areas of the vessel.

A further example may include colorizing a certain plaque component within a vessel on the output image to distinguish the certain plaque component from other items and/or areas of the vessel. In the present example, the certain plaque component is described to be lipids and the lipids are colored yellow in a three color output of red, green, and blue. However, in other examples various other plaque components can be additionally or alternatively colorized any number of colors to distinguish these components on various display color outputs. To distinguish lipids as yellow in the output image using differential frequency response, a red and green value of a red-green-blue output is calculated by multiplying (1) regions exhibiting a decrease in response at the higher frequency (determined e.g., by taking a difference between the second modified data set (including low frequency data to which the filter has been applied) and the first modified data set (including high frequency data to which the filter has been applied)) by (2) a weighting factor to obtain a product. This product can then be added to the first set of data vectors (including unmodified high frequency data), and the result is used as the calculated red and green value of the red-green-blue output. The blue value of the red-green-blue output is represented by the first set of high frequency data vectors. The result is an output image where lipids in the high frequency data set are colored yellow.

A variation on the above described example of yellow colorization of lipids may include colorizing the lipids yellow using low frequency resolution. To distinguish lipids as yellow using low frequency resolution, a red and green value of a red-green-blue output is calculated by multiplying (1) regions exhibiting a decrease in response at the higher frequency (determined e.g., by taking a difference between the second modified data set (including low frequency data to which the filter has been applied) and the first modified data set (including high frequency data to which the filter has been applied)), (2) a weighting factor, and (3) the second set of data vectors (including unmodified low frequency data) to obtain a product. This product can then be added to the first set of data vectors (including unmodified high frequency data), and the result is used as the calculated red and green value of the red-green-blue output. The blue value of the red-green-blue output is represented by the first set of high frequency data vectors. The result is an output image where lipids in the high frequency data set are colored yellow using a low resolution yellow texture.

An additional example can be utilized to create a low frequency intensity mapping included as part of the output image. For each pixel of the display at which the image is output, an intensity may be applied according to (1) dividing data from the second modified data set (e.g., low frequency data to which the filter has been applied) corresponding to the particular pixel by data from the first modified data set (e.g., high frequency data to which the filter has been applied) corresponding to the particular pixel to obtain a quotient, and (2) multiplying the resulting quotient by data corresponding to the particular pixel from the first set of data vectors (including unmodified high frequency data). Repeating this to calculate an applied intensity for each pixel of the display can result in outputting an image with a resolution of a high frequency image but advantageously having regional brightness corresponding to the second set of low frequency data vectors. Such may be facilitated by the fact that the second set of low frequency data vectors may not be affected by the otherwise resulting increase in brightness of certain items due to an increased response at the higher frequency.

In addition to visually distinguishing various items and/or regions of the vessel on the output image, other examples can provide for automatic detection of a border between two items or regions on the output image using differential frequency response of two or more items or regions. A difference between the first modified data set (e.g., high frequency data to which the filter has been applied) and the second modified data set (e.g., low frequency data to which the filter has been applied) can be calculated. The difference between the first modified data set and the second modified data set can provide an indication of regions and/or items that exhibit an increase in response at a higher frequency (e.g., blood). For each region that exhibits an increase in response at the higher frequency, a position may be located along one or more vectors corresponding to the modified data exhibiting the increase in response at the higher frequency. For instance, in one embodiment, this can be done by starting at a far end of the one or more corresponding vectors and moving inward (toward the transducer) until the position along the one or more corresponding vectors at which the increase occurs if encountered. Such one or more positions can be marked (e.g., saved). The one or more positions can then undergo one or more image processing techniques creating incongruous data at the encountered one or more positions, relative to data that has corresponds to regions that do not exhibit an increase in response at the higher frequency. A line or other indicator may then be included on an output image at positions on the output image corresponding to the incongruous data.

For instance, the presently described example for automatic border detection may be used to delineate a line at a border between blood within the vessel lumen and the start of vessel tissue defining the vessel lumen. The position at which the increase in response at the higher frequency occurs, in such an example, will be a location where the region transitions from tissue defining the vessel lumen and blood within the vessel lumen given that blood exhibits a more dynamic response to the increased frequency than the tissue defining the vessel lumen. By using the described automatic border detection, a line delineating the blood and lumen interface can be indicated on the output image and utilized, for instance, for diagnostic purposes. For example, such a line may be useful for stenosis calculations.

Embodiments also include systems that perform the method. For example, a further embodiment can include an imaging system. The system may include a catheter assembly with an intravascular imaging device (e.g., including an ultrasound transducer) to generate imaging data. The image data generated by the catheter assembly can represent a plurality of image elements. The system may also include a user interface having an image display region. In some examples, the user interface can be configured to receive inputs from a user, and may include, at least in part, one or more touchscreens. The system can further include an imaging engine in communication with the intravascular imaging device and the user interface.

The imaging engine may have at least one processor. The imaging engine can be configured to receive a plurality of first frequency data vectors and a plurality of second frequency data vectors from the catheter assembly, where the first frequency is different from the second frequency (e.g., the first frequency is greater than the second frequency). Moreover, in some cases a first frequency data vector may be emitted, and thus received, at a different time than a second frequency data vector. The imaging engine may form a first set of data vectors at the first frequency from the plurality of first frequency data vectors and a second set of data vectors at the second frequency from the plurality of second frequency data vectors using the at least one processor. The imaging engine can then, using the at least one processor, apply a filter to the first set of data vectors to produce a first modified data set as well as to the second set of data vectors to produce a second modified data set. Based on the first and second modified data sets, the imaging engine, using the at least one processor, can determine a frequency response of one or more items in an imaging view. Using the determined frequency response of one or more items in the imaging view, the imaging engine, using the at least one processor, may convey to the user interface an image for outputting on the image display region.

Another embodiment can include a non-transitory computer-readable storage article having computer-executable instructions sorted thereon to cause at least one programmable processor to convey an image based on frequency response of one or more items in an imaging view. The at least one programmable processor may receive a plurality of first and second frequency data vectors, where the first frequency is different from the second frequency (e.g., the first frequency is greater than the second frequency). Moreover, in some cases a first frequency data vector may be received at a different time than a second frequency data vector. The at least one programmable processor can form a first set of data vectors from the plurality of first frequency data vectors and a second set of data vectors from the plurality of second frequency data vectors. Additionally, a filter may be applied using the at least one programmable processor to the first set of data vectors to form a first modified data set and to the second set of data vectors to forma a second modified data set. Once the filter has been applied the at least one programmable processor can determine a frequency response of one or more items in the imaging view based on the first and second modified data sets. The at least one programmable processor may then convey an image to be output on a display based on the determined frequency response of one or more items in the imaging view.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

The invention claimed is:

1. A method for generating an intravascular ultrasound image, the method comprising the steps of:
   emitting acoustic energy from an ultrasound transducer at a first frequency and receiving a backscatter of the acoustic energy at the ultrasound transducer to acquire a plurality of first frequency data vectors representing one or more items in an imaging view at the first frequency, wherein each data vector comprises ultrasound data;
   emitting acoustic energy from the ultrasound transducer at a second frequency and receiving a backscatter of the acoustic energy at the ultrasound transducer to acquire a plurality of second frequency data vectors representing one or more items in the imaging view at the second frequency, wherein each data vector comprises ultrasound data, and wherein the first frequency is greater than the second frequency;
   forming, from the plurality of first frequency data vectors, a first set of data vectors comprising ultrasound data at the first frequency;
   forming, from the plurality of second frequency data vectors, a second set of data vectors comprising ultrasound data at the second frequency;
   applying a first filter to the first set of data vectors to form a first modified data set, wherein applying the first filter to the first set of data vectors comprises applying a smoothing filter to the first set of data vectors to form the first modified data set, wherein applying the smoothing filter to the first set of data vectors comprises constructing a first pyramid in which a first level of the first pyramid includes an image at a first resolution and a second level of the first pyramid includes the image at a second resolution, the first resolution being a greater resolution than the second resolution, wherein the image included in the first level of the first pyramid is based on the first set of data vectors and the image included in the second level of the first pyramid is based on the image included in the first level of the first pyramid;
   applying a second filter to the second set of data vectors to form a second modified data set, wherein applying the second filter to the second set of data vectors comprises applying a smoothing filter to the second set of data vectors to form the second modified data set, wherein applying the smoothing filter to the second set of data vectors comprises constructing a second pyramid in which a first level of the second pyramid includes an image at a first resolution and a second level of the second pyramid includes the image at a second resolution, the first resolution being a greater resolution than the second resolution, wherein the image included in the first level of the second pyramid is based on the second set of data vectors and the image included in the second level of the second pyramid is based on the image included in the first level of the second pyramid;
   determining a frequency response of one or more items in the imaging view based on the first and second modified data sets; and
   outputting the intravascular ultrasound image on a display based on the frequency response of one or more items in the imaging view.

2. The method of claim 1, wherein determining the frequency response of one or more items in the imaging view comprises the step of:
calculating a difference between the first modified data set and the second modified data set to ascertain whether any items in the imaging view exhibit an increase in response to the acoustic energy at the first frequency compared to the second frequency.

3. The method of claim 2, wherein determining the frequency response of one or more items in the imaging view further comprises the step of:
calculating a difference between the second modified data set and the first modified data set to ascertain whether any items in the imaging view exhibit a decrease in response to the acoustic energy at the first frequency compared to the second frequency.

4. The method of claim 3, wherein outputting the intravascular ultrasound image on the display comprises the steps of:
calculating an output value for first and second colors of a three color output, where the output value is equal to the sum of the first set of data vectors and a product of a difference between the second modified data set and the first modified data and a weighting factor; and
using the first set of data vectors as a color value for a third color of the three color output.

5. The method of claim 3, wherein outputting the intravascular ultrasound image on the display comprises the steps of:
calculating an output value for first and second colors of a three color output, where the output value is equal to the sum of 1) the first set of data vectors and 2) a product of a difference between the second modified data set and the first modified data, a weighting factor, and the second set of data vectors; and
using the first set of data vectors as a color value for a third color of the three color output.

6. The method of claim 2, further comprising using a difference between the first modified data set and the second modified data set to determine an interface between two items in the imaging view.

7. The method of claim 6, wherein the interface is determined to be the interface of a vessel border and blood within the vessel, wherein the location of blood within the vessel is determined based on the blood exhibiting an increase in response to the acoustic energy at the first frequency compared to the second frequency.

8. The method of claim 2, further comprising using an extent of the increase in response to the acoustic energy at the first frequency compared to the second frequency to differentiate blood and plaque within a vessel, and outputting the intravascular ultrasound image on the display to distinguish the blood and plaque in the image.

9. The method of claim 1, wherein acoustic energy at the first frequency is emitted and received at a same longitudinal location of the ultrasound transducer within a vessel as acoustic energy at the second frequency.

10. The method of claim 9, wherein the acquired plurality of first and second frequency data vectors are distributed circumferentially around the same longitudinal location, and wherein adjacent data vectors alternate to comprise ultrasound data at the first frequency and the second frequency.

11. The method of claim 1, wherein forming the first set of data vectors further comprises including a first number of first frequency data vectors in the first set, wherein forming the second set of data vectors further comprises including a second number of second frequency data vectors in the second set, and wherein the first number and the second number are different.

12. The method of claim 1, wherein the smoothing filter applied to the first set of data vectors is a Gaussian blur and the first pyramid is a Gaussian pyramid, and wherein the smoothing filter applied to the second set of data vectors is a Gaussian blur and the second pyramid is a Gaussian pyramid.

13. The method of claim 1, wherein applying the second filter to the second set of data vectors further comprises the step of:
applying a sharpening filter to the second set of data vectors after applying the smoothing filter.

14. The method of claim 12, wherein
applying the first filter to the first set of data vectors further comprises applying a sharpening filter after applying the smoothing filter to construct a first Laplacian pyramid based on the first Gaussian pyramid; and
applying the second filter to the second set of data vectors further comprises applying a sharpening filter after applying the smoothing filter to construct a second Laplacian pyramid based on the second Gaussian pyramid.

15. The method of claim 14, wherein outputting the intravascular ultrasound image on the display comprises constructing the intravascular ultrasound image based on a combination of the first and second Laplacian pyramids.

16. A method for generating an intravascular ultrasound image, the method comprising the steps of:
emitting acoustic energy from an ultrasound transducer at a first frequency and receiving a backscatter of the acoustic energy at the ultrasound transducer to acquire a plurality of first frequency data vectors representing one or more items in an imaging view at the first frequency, wherein each data vector comprises ultrasound data;
emitting acoustic energy from the ultrasound transducer at a second frequency and receiving a backscatter of the acoustic energy at the ultrasound transducer to acquire a plurality of second frequency data vectors representing one or more items in the imaging view at the second frequency, wherein each data vector comprises ultrasound data, wherein acoustic energy at the first frequency is emitted at a different time than acoustic energy at the second frequency, and wherein the first frequency is greater than the second frequency;
forming, from the plurality of first frequency data vectors, a first set of data vectors comprising ultrasound data at the first frequency;
forming, from the plurality of second frequency data vectors, a second set of data vectors comprising ultrasound data at the second frequency;
applying a first filter comprising a smoothing filter to the first set of data vectors to form a first modified data set;
applying a second filter comprising a smoothing filter to the second set of data vectors to form a second modified data set;
applying a sharpening filter to the second set of data vectors after applying the smoothing filter;
determining a frequency response of one or more items in the imaging view based on the first and second modified data sets; and
outputting the intravascular ultrasound image on a display based on the frequency response of one or more items in the imaging view.

17. The method of claim 16, wherein determining the frequency response of one or more items in the imaging view comprises the step of:
calculating a difference between the first modified data set and the second modified data set to ascertain whether any items in the imaging view exhibit an increase in response to the acoustic energy at the first frequency compared to the second frequency.

18. The method of claim 16, wherein the first modified data set includes a lower resolution than the first set of data vectors, and wherein the second modified data set includes a lower resolution than the second set of data vectors.

19. The method of claim 16, wherein outputting the intravascular ultrasound image on the display comprises:
applying an intensity output for a pixel on the display where the intensity output for the pixel is calculated by dividing the second modified data set by the first modified data set to obtain a quotient and multiplying the quotient by the first set of data vectors.

20. A method for generating an intravascular ultrasound image, the method comprising the steps of:
emitting acoustic energy from an ultrasound transducer at a first frequency and receiving a backscatter of the acoustic energy at the ultrasound transducer to acquire a plurality of first frequency data vectors representing one or more items in an imaging view at the first frequency, wherein each data vector comprises ultrasound data;
emitting acoustic energy from the ultrasound transducer at a second frequency and receiving a backscatter of the acoustic energy at the ultrasound transducer to acquire a plurality of second frequency data vectors representing one or more items in the imaging view at the second frequency, wherein each data vector comprises ultrasound data, wherein acoustic energy at the first frequency is emitted at a different time than acoustic energy at the second frequency, and wherein the first frequency is greater than the second frequency;
forming, from the plurality of first frequency data vectors, a first set of data vectors comprising ultrasound data at the first frequency;
forming, from the plurality of second frequency data vectors, a second set of data vectors comprising ultrasound data at the second frequency;
applying a first filter comprising a smoothing filter to the first set of data vectors to form a first modified data set;
applying a second filter comprising a smoothing filter to the second set of data vectors to form a second modified data set;
determining a frequency response of one or more items in the imaging view based on the first and second modified data sets;
outputting the intravascular ultrasound image on a display based on the frequency response of one or more items in the imaging view; and
applying an intensity output for a pixel on the display where the intensity output for the pixel is calculated by dividing the second modified data set by the first modified data set to obtain a quotient and multiplying the quotient by the first set of data vectors.

21. A method for generating an intravascular ultrasound image, the method comprising the steps of:
emitting acoustic energy from an ultrasound transducer at a first frequency and receiving a backscatter of the acoustic energy at the ultrasound transducer to acquire a plurality of first frequency data vectors representing one or more items in an imaging view at the first frequency, wherein each data vector comprises ultrasound data;
emitting acoustic energy from the ultrasound transducer at a second frequency and receiving a backscatter of the acoustic energy at the ultrasound transducer to acquire a plurality of second frequency data vectors representing one or more items in the imaging view at the second frequency, wherein each data vector comprises ultrasound data, wherein acoustic energy at the first frequency is emitted at a different time than acoustic energy at the second frequency, and wherein the first frequency is greater than the second frequency;
forming, from the plurality of first frequency data vectors, a first set of data vectors comprising ultrasound data at the first frequency;
forming, from the plurality of second frequency data vectors, a second set of data vectors comprising ultrasound data at the second frequency;
applying a first filter comprising a smoothing filter to the first set of data vectors to form a first modified data set;
applying a second filter comprising a smoothing filter to the second set of data vectors to form a second modified data set;
determining a frequency response of one or more items in the imaging view based on the first and second modified data sets, wherein determining the frequency response of one or more items in the imaging view comprises calculating a difference between the first modified data set and the second modified data set to ascertain whether any items in the imaging view exhibit an increase in response to the acoustic energy at the first frequency compared to the second frequency; and
outputting the intravascular ultrasound image on a display based on the frequency response of one or more items in the imaging view, wherein outputting the intravascular ultrasound image on the display comprises applying an intensity output for a pixel on the display where the intensity output for the pixel is calculated by multiplying a difference between the first modified data set and the second modified data set by a weighting factor to obtain a product and subtracting the product from the first set of data vectors.

22. The method of claim 21, further comprising using the applied intensity output for the pixel on the display as a color value for first and second colors of a three color output, and using the first set of data vectors as a color value for a third color of the three color output.

* * * * *